(12) United States Patent
Oshiki et al.

(10) Patent No.: US 9,007,872 B2
(45) Date of Patent: Apr. 14, 2015

(54) ULTRASONIC DIAGNOSTIC APPARATUS AND METHOD THEREOF

(75) Inventors: Mitsuhiro Oshiki, Tokyo (JP); Atsushi Suzuki, Tokyo (JP); Kanako Hatayama, Tokyo (JP); Kenji Maio, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 919 days.

(21) Appl. No.: 13/148,306

(22) PCT Filed: Feb. 2, 2010

(86) PCT No.: PCT/JP2010/051367
§ 371 (c)(1),
(2), (4) Date: Oct. 24, 2011

(87) PCT Pub. No.: WO2010/090160
PCT Pub. Date: Aug. 12, 2010

(65) Prior Publication Data
US 2012/0113759 A1 May 10, 2012

(30) Foreign Application Priority Data
Feb. 6, 2009 (JP) ................................. 2009-026066

(51) Int. Cl.
| | | |
|---|---|---|
| G01S 3/80 | (2006.01) | |
| A61B 8/00 | (2006.01) | |
| G01N 29/24 | (2006.01) | |
| G01N 29/26 | (2006.01) | |
| G01S 7/52 | (2006.01) | |
| G10K 11/34 | (2006.01) | |
| G01S 15/89 | (2006.01) | |

(52) U.S. Cl.
CPC ...... *A61B 8/00* (2013.01); *G01N 29/24* (2013.01); *G01N 29/262* (2013.01); *G01S 7/52019* (2013.01); *G01S 7/5208* (2013.01); *G10K 11/346* (2013.01); *G01S 15/8915* (2013.01)

(58) Field of Classification Search
CPC .... A61B 8/12; G01S 7/52034; G01S 15/8915
USPC ................................... 367/127; 600/300, 437
See application file for complete search history.

(56) References Cited

U.S. PATENT DOCUMENTS 5,301,167 A * 4/1994 Proakis et al. ................. 367/134
5,590,658 A * 1/1997 Chiang et al. ................. 600/447

(Continued)

FOREIGN PATENT DOCUMENTS

JP 2005-152450 6/2005
JP 2007-325937 12/2007

(Continued)

*Primary Examiner* — Luke Ratcliffe
*Assistant Examiner* — Hovhannes Baghdasaryan
(74) *Attorney, Agent, or Firm* — Brundidge & Stanger, P.C.

(57) ABSTRACT

An ultrasonic diagnostic apparatus characterized by comprising, a probe which has a transducer and which transmits and receives ultrasonic waves, an ultrasonic diagnostic apparatus main body; and a cable through which signals are transmitted and received between the ultrasonic diagnostic apparatus main body and the probe, wherein the probe includes a transmission signal generator that generates an ultrasonic transmission signal, a transmission circuit that amplifies the generated transmission signal, and a transmission phasing circuit that adjusts the timing of the transmission signal.

13 Claims, 11 Drawing Sheets

(56) References Cited

U.S. PATENT DOCUMENTS

| | | | |
|---|---|---|---|
| 6,072,427 A * | 6/2000 | McEwan | 342/175 |
| 2005/0148872 A1 * | 7/2005 | Richard | 600/443 |
| 2005/0148874 A1 * | 7/2005 | Brock-Fisher et al. | 600/447 |
| 2007/0083119 A1 * | 4/2007 | Adachi et al. | 600/437 |
| 2007/0232893 A1 * | 10/2007 | Tanioka | 600/407 |
| 2009/0005683 A1 * | 1/2009 | Hashimoto et al. | 600/443 |

FOREIGN PATENT DOCUMENTS

| | | |
|---|---|---|
| JP | 2008-259891 | 10/2008 |
| WO | 2005/120359 | 12/2005 |

\* cited by examiner

ULTRASONIC DIAGNOSTIC APPARATUS AND METHOD THEREOF

TECHNICAL FIELD

The invention relates to an ultrasonic diagnostic apparatus. More particularly, the invention relates to an ultrasonic diagnostic apparatus in which a probe that transmits and receives ultrasonic waves includes a transmission signal generator including a transmission circuit that drives a transducer, a transmission waveform storage memory, and the like, and a transmission phasing function is incorporated into the probe, so that an analog signal line through which a high-voltage transmission signal is transmitted from the device main body to the probe is not necessary.

BACKGROUND ART

An ultrasonic diagnostic apparatus is a device that applies a voltage to a transducer mainly formed of a piezoelectric material, transmits ultrasonic waves generated by the transducer to a subject, and extracts various kinds of information from the reflection waves to thereby obtain internal information of the subject.

In the related art, a number of transmission circuits that apply a voltage to transducers are formed in a device main body, and the number corresponds to the number of phasing bores which is generally several tens of channels. If the number of transducers in a probe is greater than the number of phasing bores, one channel of the transmission circuits and a plurality of transducers are used by being switched by a switch that is provided in the device.

Moreover, in recent years, a 2-dimensional array ultrasonic probe in which transducers are arranged 2-dimensionally has been developed. If the transducers are arranged in a 32-by-32 arrangement, the total number of transducers becomes 1024. Thus, when all transducers are driven, a matrix-type switch or the like which requires complex control needs to be provided between the driving transducers and the transmission circuits of several tens of channels provided in the device main body.

However, such a configuration is not practical because the input capacitance or the like of the switch causes a problem. Thus, it is necessary to take measures such as limiting the transducers driven by the respective transmission circuits to a certain number of effective transducers. In all cases, it is necessary to control the matrix-type switch which requires complex control.

As described above, in the related art, in order to drive many transducers, it is necessary to transmit a number of analog transmission signals, which correspond to the number of transmission circuits and which have sufficient amplitude necessary for obtaining a diagnostic image, from an ultrasonic diagnostic apparatus main body to the probe through a cable.

Patent Literature 1 discloses an invention relating to a transmission circuit which can be incorporated into a probe.

In the transmission circuit disclosed in Patent Literature 1, the transmission circuit is configured as a switch to decrease the size thereof so as to be incorporated into a probe. By doing so, it may be not necessary to transmit an analog signal having large amplitude from the ultrasonic diagnostic apparatus main body.

However, a number of signal lines for transmitting transmission input signals corresponding to the number of transmission circuits need to be included in the cable.

Moreover, it is still necessary to use a changeover switch in order to absorb the difference in number between the transmission circuits and the transducers.

Furthermore, Patent Literature 1 does not have any description a method of controlling the internal transmission circuits from the side of the main body of the ultrasonic diagnostic apparatus, the relation of the numbers of transmission circuits and transducers, and transmission phasing.

In addition, Patent Literature 2 discloses an invention relating to control of delay in transmission phasing. Specifically, Patent Literature 2 discloses transmission means having means for controlling the transmission timing of an ultrasonic wave signal with a precision that is ¼ of a sampling clock cycle used for actual transmission by using 4-phase clock signals which are delayed in time with respect to a principal clock.

However, the proposal cannot realize a delay corresponding to finer precision since the delay precision is fixed to ¼ of the sampling clock cycle.

CITATION LIST

Patent Literature

PTL 1: U.S. Pat. No. 7,022,074
PTL 2: JP-A-2006-288851

SUMMARY OF THE INVENTION

Technical Problem

As described above, although an invention relating to incorporation of transmission circuits into a probe is known in the related art, the invention does not disclose the specific control method and a technique of incorporating a transmission phasing function into the probe.

Moreover, in the invention known in the related art, the number of signal lines through which signals are transmitted from the diagnostic device main body to the probe increases as the number of incorporated transmission circuits increases.

Furthermore, although there are many transducers, the transducers capable of actually transmitting ultrasonic wave signals are limited to the number of transmission circuits smaller than the number of transducers.

An object of the invention is to provide an ultrasonic diagnostic apparatus in which circuits such as a transmission signal generator and a transmission circuit can be incorporated into a probe, thus making it unnecessary to transmit a high-voltage signal from an ultrasonic diagnostic apparatus main body and further decreasing the number of transmission cables to less than that required in the related art.

Solution to Problem

The invention provides an ultrasonic diagnostic apparatus including a probe which has a transducer and which transmits and receives ultrasonic waves; an ultrasonic diagnostic apparatus main body; and a cable through which signals are transmitted and received between the ultrasonic diagnostic apparatus main body and the probe, wherein the probe includes a transmission signal generator that generates an ultrasonic transmission signal; a transmission circuit that amplifies the generated transmission signal; and a transmission phasing circuit that adjusts the timing of the transmission signal.

The transmission signal generator is configured by a memory, for example, a shift register, that stores transmission signal waveforms. The transmission waveforms are written in advance in the shift register and may be transmitted from the ultrasonic diagnostic apparatus main body or the like to the shift register in the probe whenever transmission is performed. In order to form a beam at a desired focus point, it is necessary to apply a delay time to each transducer that transmits ultrasonic waves. A clock signal having a phase condition corresponding to a unique delay time is applied to each transducer, and a transmission waveform is read from the shift register and transmitted to the transmission circuit. The transmission waveform is amplified to an amplitude level sufficient for driving the transducer and is then applied to the transducer, whereby an ultrasonic wave signal is obtained.

The unique clock timing having phasing information determined for each driving transducer is set in advance or is determined based on focus data which is calculated internally. The delay in units of a transmission clock can be realized by delaying the readout timing of the shift register, and the delay equal to or smaller than the transmission clock unit is generated by a DLL (Delay Locked Loop) circuit, for example.

Therefore, the signals which need to be transmitted from the device main body to the probe include only a power supply which drives the transmission circuit, a transmission clock, and waveform data. Accordingly, transmission amplification having the transmission phasing function can be realized within the probe.

Moreover, since the delay signal is created by the DLL circuit, it is not necessary to use a high-speed clock and it is possible to realize a transmission phasing circuit at a low cost and with a simple circuit configuration.

Moreover, in the ultrasonic diagnostic apparatus of the invention, the probe may have a plurality of transducers, and the transmission signal generator, the transmission circuit, and the transmission phasing circuit may be independently provided to each transducer.

In the ultrasonic diagnostic apparatus, since it is possible to apply an independent phasing condition to each transducer, it is possible to form an acoustic field using all transducers of the probe unlike the related art where the number of transducers is limited by the number of transmission channels of the device main body side.

As a result, in the invention, it is not necessary to use a changeover switch which is required in the ultrasonic diagnostic apparatus of the related art in order to absorb the difference in total numbers of the transmission circuits and the transducers which are more than the number of transmission circuits. Therefore, it is possible to eliminate signal attenuation due to the resistance component of switches, and a change in the transmission/reception signal waveform due to phase rotation or the like caused by the capacitance component.

Moreover, in the ultrasonic diagnostic apparatus of the invention, no analog transmission cable is provided between the ultrasonic diagnostic apparatus main body and the probe.

Since the signals input to the probe having the transmission circuit of the invention include only the power supply, the transmission clock, and waveform data as necessary, the high-voltage analog signal lines which are provided for transmission channels between the device main body and the transducers in the related art are not needed. Moreover, since digital communication is possible, it is possible to decrease the number of transmission cables.

Furthermore, since transmission of a high-voltage analog signal is not necessary, data can be transmitted wirelessly from the device main body to the probe of the present application.

Advantageous Effects of the Invention

As described above, according to the invention, a transmission phasing circuit, a transmission signal generator, and a transmission circuit can be incorporated into a probe of an ultrasonic diagnostic apparatus. In this way, it is not necessary to transmit a high-voltage signal from the main body of the ultrasonic diagnostic apparatus.

Moreover, since the device main body only needs to transmit a principal clock, a power supply, and a digital transmission signal through a data bus, it is not necessary to transmit an analog transmission signal. Thus, it is possible to decrease the number of transmission cables corresponding to the number of transmission circuits required in the related art.

DESCRIPTION OF EMBODIMENTS

Hereinafter, preferred embodiments of the invention will be described with reference to the drawings. However, the invention is not limited to the embodiments.

First Embodiment

Figure 1:
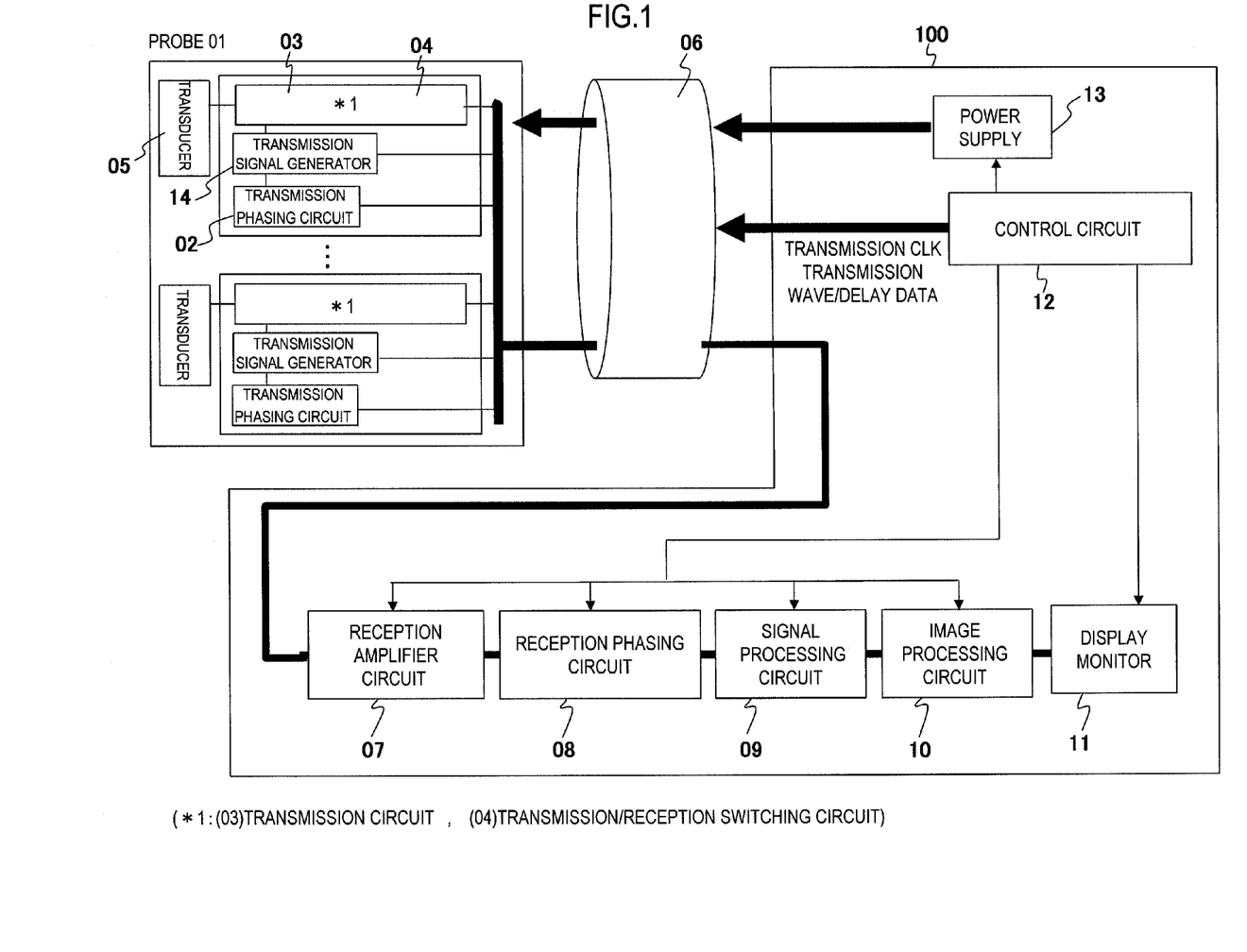
FIG. 1 is a block diagram of an ultrasonic diagnostic apparatus according to a first embodiment of the invention.

FIG. 1 shows an ultrasonic diagnostic apparatus according to a first embodiment of the invention.

The circuit is configured to include a probe 01, a cable 06, and an ultrasonic diagnostic apparatus main body 100. The probe 01 includes a transducer 05, a transmission phasing circuit 02, a transmission circuit 03, a transmission signal generator 14, and a transmission/reception switching circuit 04. Moreover, a reception amplifier circuit 07, a reception phasing circuit 08, a signal processing circuit 09, an image processing circuit 10, and a display monitor 11 are provided in the main body 100.

The main body 100 also includes a control circuit 12 and a power supply 13.

The transducer 05 is formed so as to have a function of converting a transmission signal input from the transmission circuit 03 in the form of pulse waves or continuous waves into ultrasonic waves and transmitting the ultrasonic waves to a subject and a function of receiving ultrasonic waves reflected from the inner part of the subject and converting and outputting the ultrasonic waves into electrical signals.

The transmission phasing circuit 02 is configured to adjust the timing of applying a voltage to each driving transducer so as to be different for each of the transducers when forming transmission beams on a subject. In general, the timing is controlled so that a voltage is applied to a transducer located farther from a focusing position at an earlier time than other driving transducers.

The transmission circuit 03 is configured to amplify a transmission signal waveform formed by the transmission signal generator 14 to a magnitude sufficient for driving the transducer 05 and generating an ultrasonic wave signal and to output the amplified transmission signal waveform.

The transmission signal generator 14 is configured to determine the shape of a transmission waveform. For example, the transmission signal generator 14 includes a memory in which one or plural transmission waveforms are stored. The waveform can be selected by the control circuit 12 of the ultrasonic diagnostic apparatus main body 100. Alternatively, whenever the transmission signal is generated, the waveform may be transferred from the ultrasonic diagnostic apparatus main body 100 through the cable 06 and stored.

The transmission/reception switching circuit 04 is configured to switch a signal path on the circuit when a transmission signal transmitted by the transmission circuit 03 and a reception signal which is an ultrasonic wave signal transmitted by the transducer 05 driven by the transmission signal and which is reflected from a target object are guided to the reception amplifier circuit 07. In this way, the signal from the transmission circuit 03 can be transmitted to the transducer without being applied to the reception amplifier circuit 07, and the signal from the subject can be guided to the reception amplifier circuit 07 through the transducer without being affected by the transmission circuit 03.

The reception amplifier circuit 07 has a function of amplifying the ultrasonic wave signal obtained from the subject and changing the amplification factor each time.

The reception phasing circuit 08 has a function of forming beams similarly to the transmission phasing circuit 02. The reception phasing circuit 08 is configured to adjust the timing of adding signals from all transducers obtaining signals from the subject so as to be different for each of the transducers when forming reception beams. The delay time for a transducer located closer to a focus position is increased to be greater than other transducers so as to match the timing of adding the reception signals obtained by transducers located farther from the focus position.

The signal processing circuit 09 and the image processing circuit 10 are configured to perform signal processing of converting the signal obtained through phasing addition into luminance information through wave detection or the like and perform coordinate conversion processing in accordance with the type of a probe through image signal processing as typified by γ processing. Here, the processed signal is displayed on the display monitor 11 as a diagnostic image.

Moreover, the above-described respective constituent circuits receive a principal clock signal from the control circuit 12, and the timings of respective portions or the like are controlled. Specifically, transmission/reception switching is controlled and a diagnostic mode is switched.

Moreover, the power supply 13 is controlled by the control circuit 12 so as to generate various voltage values. Here, the generated voltage having various values is supplied to respective circuit units although not shown in the figure.

Figure 4:
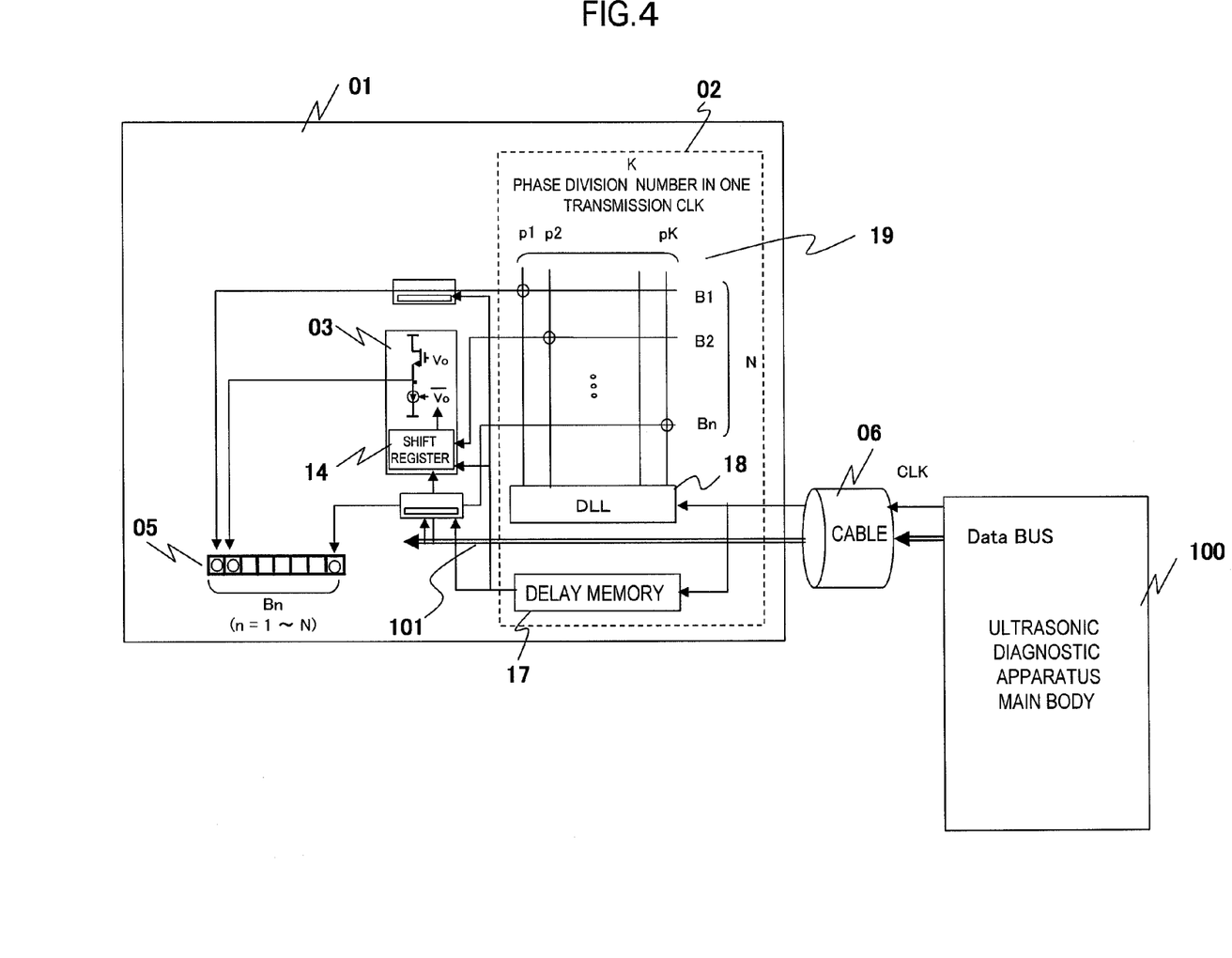
FIG. 4 is a block diagram showing a circuit incorporated in a probe of the ultrasonic diagnostic apparatus according to the invention.

FIG. 4 shows a detailed block diagram of a characteristic portion of the invention.

The ultrasonic diagnostic apparatus shown in FIG. 4 includes the probe 01, the ultrasonic diagnostic apparatus main body 100, and the cable 06 connecting them together.

The transmission signal generator 14 is configured by a shift register, for example. Data may be written in advance to the shift register, and alternatively, data may be periodically transmitted from the ultrasonic diagnostic apparatus main body 100 through a data bus 101 and written to the shift register. Alternatively, a plurality of transmission waveforms may be written to the shift register or may be periodically transmitted by the ultrasonic diagnostic apparatus main body 100, and the control circuit 12 may select one from the plurality of transmission waveforms.

The transmission circuit 03 receives a transmission signal which is generated and determined by the transmission signal generator 14, amplifies the transmission signal, and drives the transducer 05. The driving timing is determined by the transmission phasing circuit 02.

In this embodiment, the transmission phasing circuit 02 is configured to include a delay memory 17, a DLL circuit 18, and a selector circuit 19.

Figure 5:
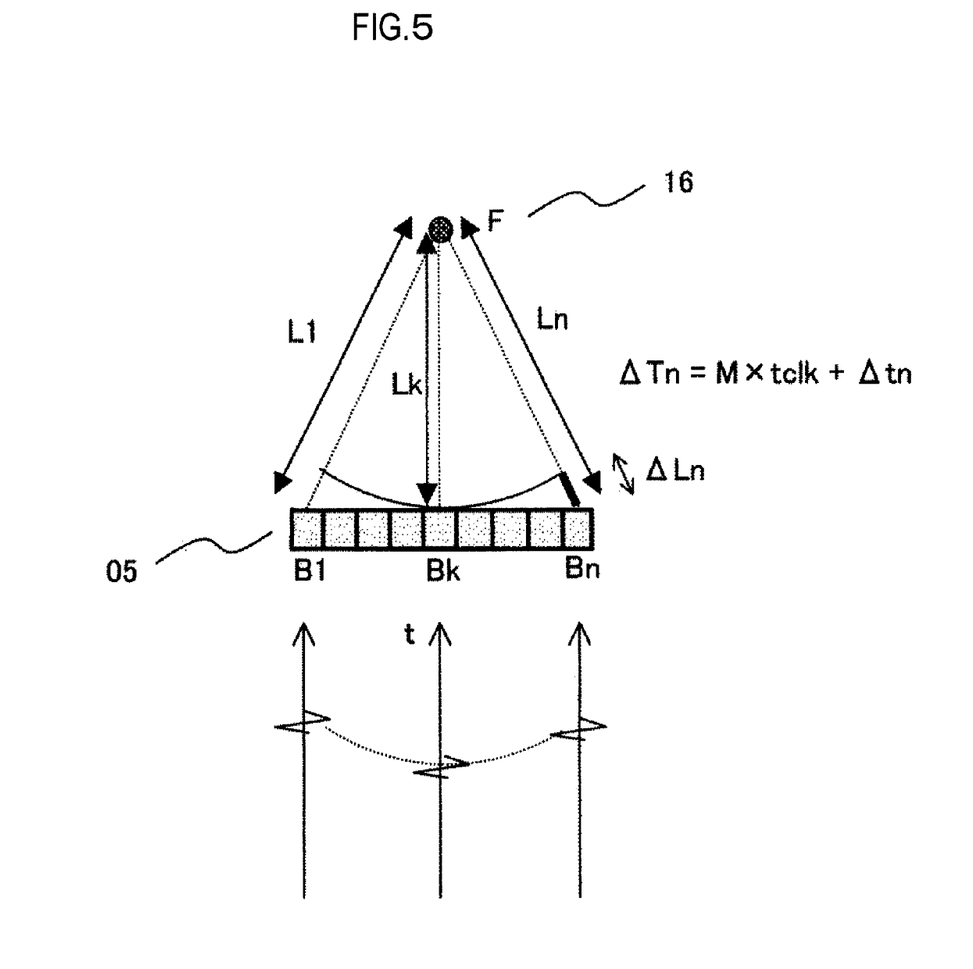
FIG. 5 is a diagram showing the principle of rectifying the transmission wave phase in the ultrasonic diagnostic apparatus.

FIG. 5 illustrates the principle of transmission phasing. It is assumed that the transducer 05 is made up of an array of n transducers B1 to Bn. If a focus point 16 of a beam is denoted by F, the distances from the respective transducers to the focus point F can be expressed as L1 to Ln.

It is assumed that a transducer closest to the focus point among the n transducers is Bk, and the distance from the transducer to the focus point is Lk. The difference $\Delta Ln$ of the distances from the respective transducers to the focus point F with reference to Lk can be expressed as follows.

$$\Delta Ln = Ln - Lk \quad \text{(Expression 1)}$$

In order to arrange the signals from the respective transducers at the focus point F so as to have the same phase, it is necessary to control the signal driving timings for each transducer while taking the difference $\Delta Ln$ into account. Specifically, when the transducers Bk and Bn are driven at the same phase, a signal from the transducer Bn may be $\Delta Ln$ ahead of the focus point F when a signal from the transducer Bk reaches the focus point F. Thus, it is necessary to advance the driving timing of the signal from the transducer Bn by a period corresponding to $\Delta Ln$.

Here, if the velocity of sound in a subject is vsound, the following expressions are obtained.

$$\Delta Ln = \Delta Tn \times v\text{sound} \quad \text{(Expression 2)}$$

$$\Delta Tn = M \times tclk + \Delta tn \quad \text{(Expression 3)}$$

Here, $\Delta Tn$ is a sonic wave propagation time taken for a sonic wave to propagate from the respective transducers Bn to the focus point F, tclk is the cycle of a principal clock output from the control circuit 12 of the ultrasonic diagnostic apparatus main body, and M is an integer. Moreover, $\Delta tn$ represents a period equal to or smaller than the principal clock cycle tclk.

In this example, since the transducer Bn is located farther from the focus point F by a distance of $\Delta Ln$ than the reference transducer Bk, the transducer Bn needs to be driven earlier than the transducer Bk by an amount of $\Delta Tn$. The amount $\Delta Tn$ corresponds to the sum of M principal clock intervals and $\Delta tn$ in the ultrasonic diagnostic apparatus of the present embodiment.

Given the above, it is necessary to advance the operation timing of the transmission circuit 03 connected to the transducer Bn by an amount of $\Delta Tn$. Thus, the clock supplied to the transmission signal generator 14 configured, for example, by a shift register and connected to the transducer Bn may be moved forward by an amount of ΔTn as compared to that of the transducer Bk.

As a result, in order to transmit in-phase signals from a plurality of transducers to the same focus point 16, it is necessary to apply a value in units of the principal clock tclk and a micro period equal to or smaller than the principal clock as a delay time. The delay time will be referred to as focus data.

(Focus Data)=(Principal Clock)×M+(Micro Delay)  (Expression 4)

where, M=0, 1, 2, . . . integer

As shown in FIG. 4, in the present embodiment, the delay amount in units of the principal clock is handled in the delay memory 17. Similarly to transmission of data to the shift register, the delay amount may be written in advance to the delay memory 17, and may be transmitted from the ultrasonic diagnostic apparatus main body 100 at arbitrary timing. The delay amount may be stored in advance in an internal memory (not shown) of the ultrasonic diagnostic apparatus main body 100, and may be calculated in the control circuit 12.

In addition, the control of the delay amount in units of the principal clock may not be performed depending on the position of the transmission focus. For example, when the focus position is located at a sufficient distance position as compared to the pitch of transducers, the time offset between the adjacent elements becomes equal to or smaller than the principal clock. Thus, it is not necessary to take a delay according to this degree of precision into account. In this case, 0 is stored in the delay memory 17 as delay data.

Since the delay data is different depending on the focus position, the control circuit 12 gives an instruction as to whether or not to use the data whenever focusing is performed.

Moreover, the micro delay which is a delay time equal to or smaller than the principal clock tclk is generated in the transmission phasing circuit 02. A more preferred embodiment will be described with reference to the drawings.

Figure 6:
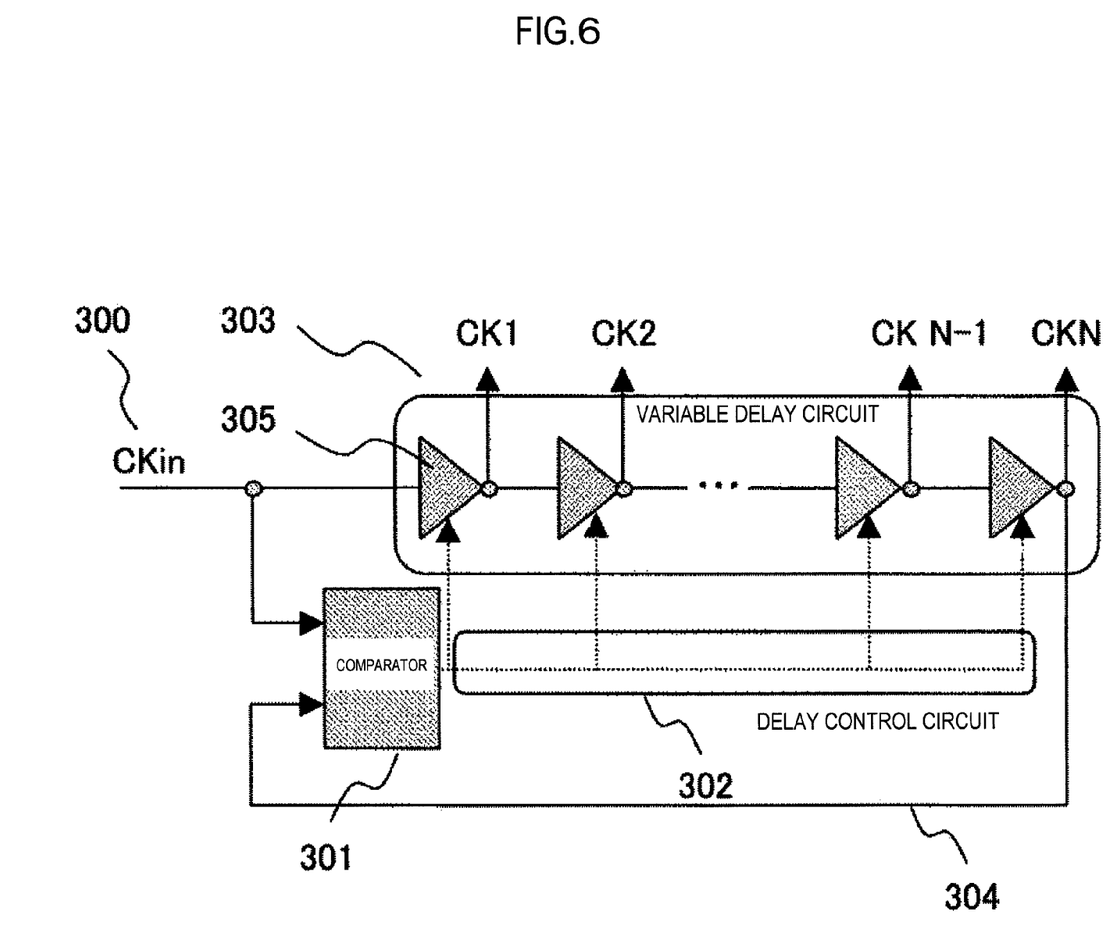
FIG. 6 is a diagram showing a micro delay circuit using a DLL circuit.

FIG. 6 illustrates a method of creating a micro delay by way of a schematic diagram of a DLL (Delay Locked Loop) circuit. The DLL circuit includes a signal input portion 300 (Ckin), a phase comparator 301, a delay control circuit 302, and a variable delay circuit 303. A delay amount of the variable delay circuit 303 is determined by a value that is output by the delay control circuit 302.

The phase comparator 301 compares the phase of a signal input from the signal input portion 300 and the phase of a feedback signal 304 fed back from the variable delay circuit and outputs the comparison result to the delay control circuit 302. The delay control circuit outputs the value held therein to the variable delay circuit 303 to thereby control the delay amount of the variable delay circuit 303.

Moreover, the delay control circuit 302 controls the delay amount so as to eliminate a phase offset based on the comparison result output by the phase comparator 301, between the phase of the signal input from a clock signal input portion 300 and the phase of the feedback signal 303.

An example of the configuration of the variable delay circuit is also shown in FIG. 6. In the figure, the variable delay circuit 303 delays the signal input from the signal input portion 300 using a chain of N series-connected by delay elements 305 configured by inverters, for example.

In the configuration of FIG. 6, since there are N delay stages, it is possible to control the delay as finely as N divisions of the input clock (Ckin).

A more specific example will be described with reference to FIG. 7.

Figure 7:
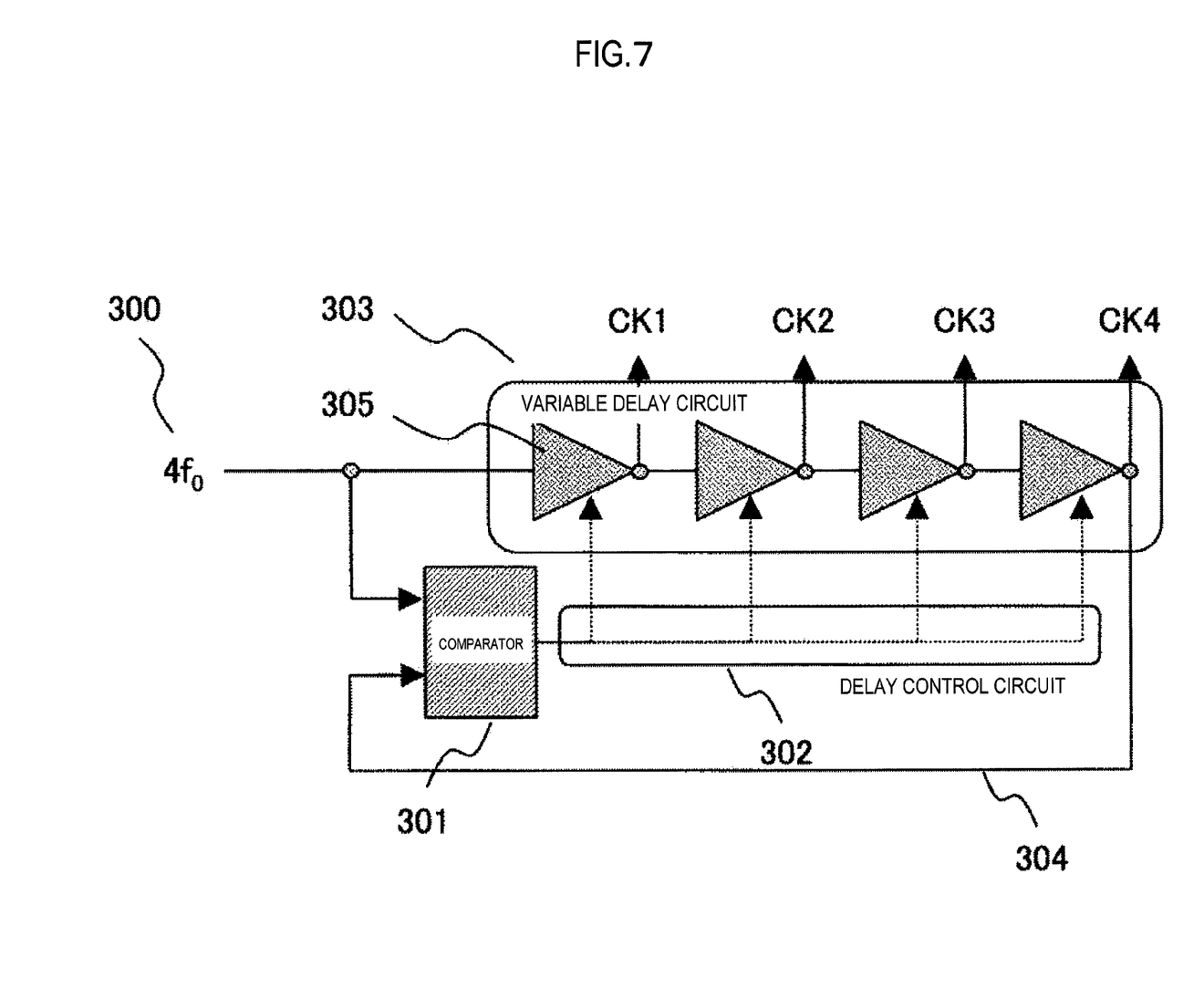
FIG. 7 is a diagram showing a micro delay circuit using a DLL circuit.
Figure 8:
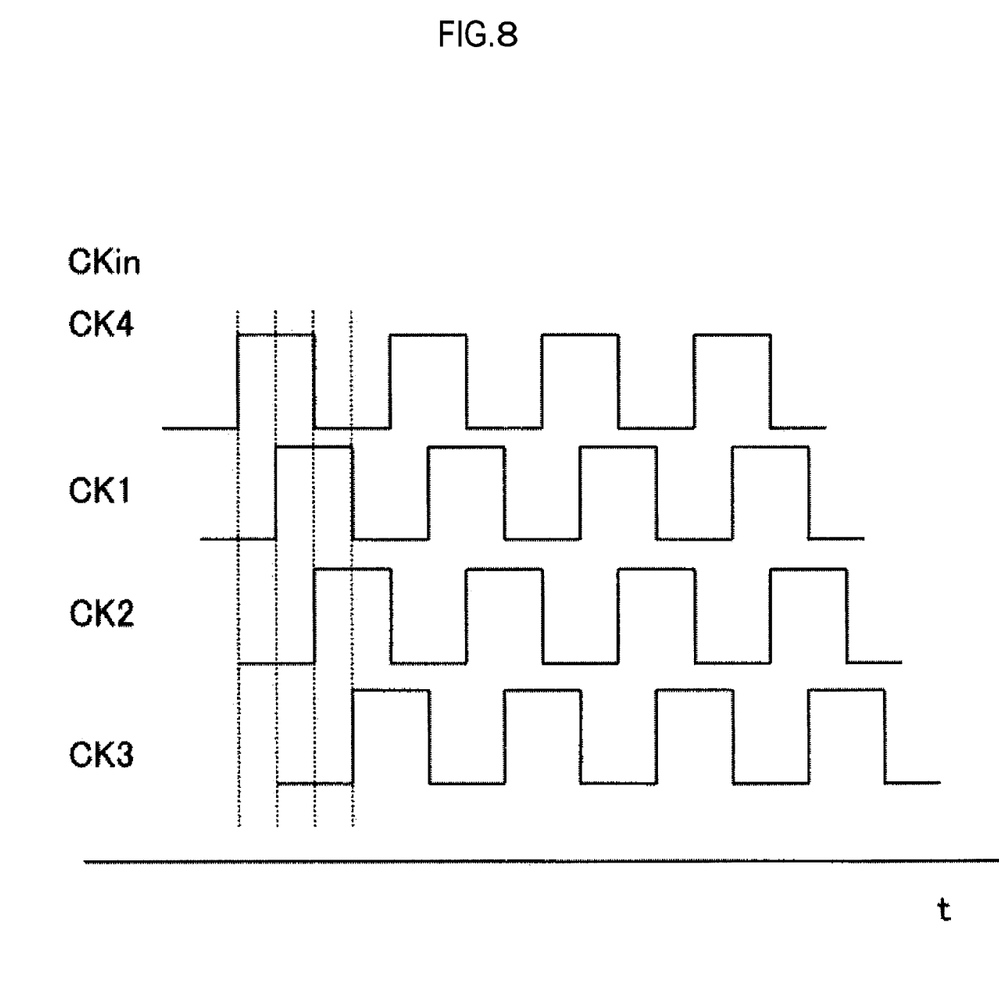
FIG. 8 is a diagram showing the output of the DLL circuit shown in FIG. 7.

FIG. 7 shows a case where the number of delay stages is 4. In FIG. 8, CKin which is the clock signal input from the signal input portion 300 is shown on the top. Since there are four stages of delay elements, the respective delay elements can output the signals CKin with the phases shifted by 360°/4=90°. Therefore, as shown in FIG. 8, the signals CK1 to CK3 are output with the phases shifted by 90°. When the input clock signal is a continuous wave, the signal CK4 is output to be superimposed on the input signal.

Figure 9:
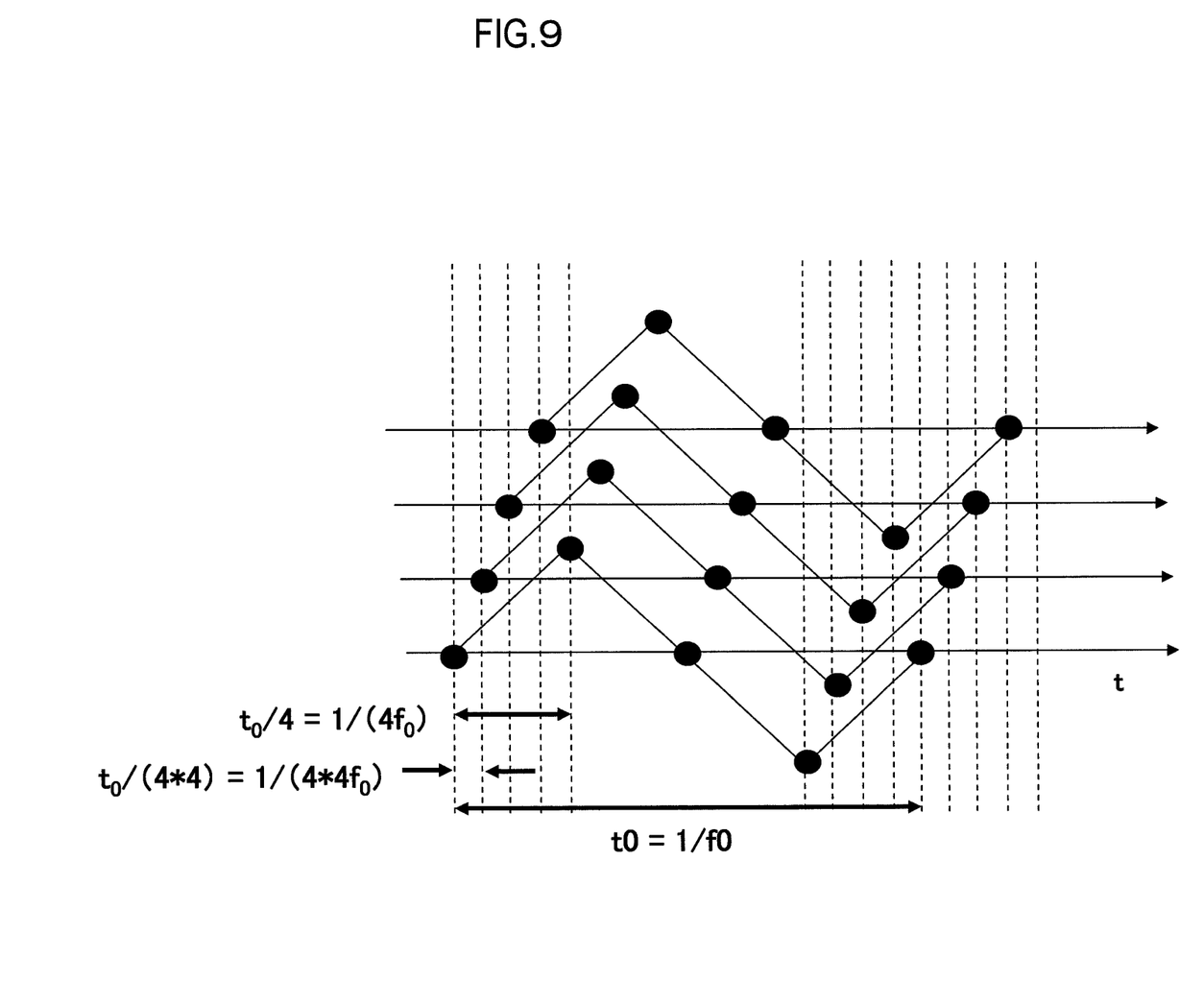
FIG. 9 is a diagram showing a delayed transmission signal output by the DLL circuit shown in FIG. 7.

A more preferred embodiment will be described with reference to FIG. 9. FIG. 9 shows a state in which the transmission signal output from the shift register 14 described above is delayed. FIG. 9 shows a case in which waveform data for one cycle is stored in the shift register 14 as the transmission signal. Since the transmission signal is output in synchronization with the timing of the clock signal input to the shift register, in order to delay the transmission signal, the clock input to the shift register may be delayed.

It is assumed that a clock having a frequency four times the frequency f0 of the transmission signal is input to the signal input portion 300. Here, as shown in FIG. 7, when there are four delay elements, delay precision of f0×4×4 (16×f0) is obtained.

It is assumed that f0 is 5 MHz, and the sampling clock of the device is 20 MHz. In this case, the distance between the black circles in FIG. 9 is the principal clock of the device, and the maximum sampling cycle becomes 20 MHz. However, in the delay insertion configuration using the DLL, as shown in FIG. 8, since it provides delay precision that is four times the principal clock, it is possible to provide delay precision of up to 16×f0=80 MHz. Thus, as shown in FIG. 9, in this example, it is possible to provide a delay corresponding to a cycle that is four times finer than the sampling cycle of the device as denoted by the black circles. Thus, it is possible to realize a sensitive clock delay through the design of a DLL delay circuit, and the delay clock is supplied to the shift register 14 shown in FIG. 4.

As described above, since the delay signal is obtained using the DLL circuit, it is not necessary to use a high-speed clock signal and it is possible to realize a transmission phasing function at a low cost and with a simple circuit configuration.

As described above, the delay amount is changed for each of all transducers used when forming beams. Thus, it is necessary to apply a unique value to each transducer. In the transmission phasing circuit 02 shown in FIG. 4, it is necessary to realize an n-by-k matrix configuration where n is the number of connected transducers and k is the number of divisions for clock delay.

(Number of Transducers:n)×(Number of Clock Divisions:k)  (Expression 5)

The output of the matrix constituting the selector circuit 19 is connected to the transmission signal generator 14 of each transducer as shown in FIG. 4.

Figure 10:
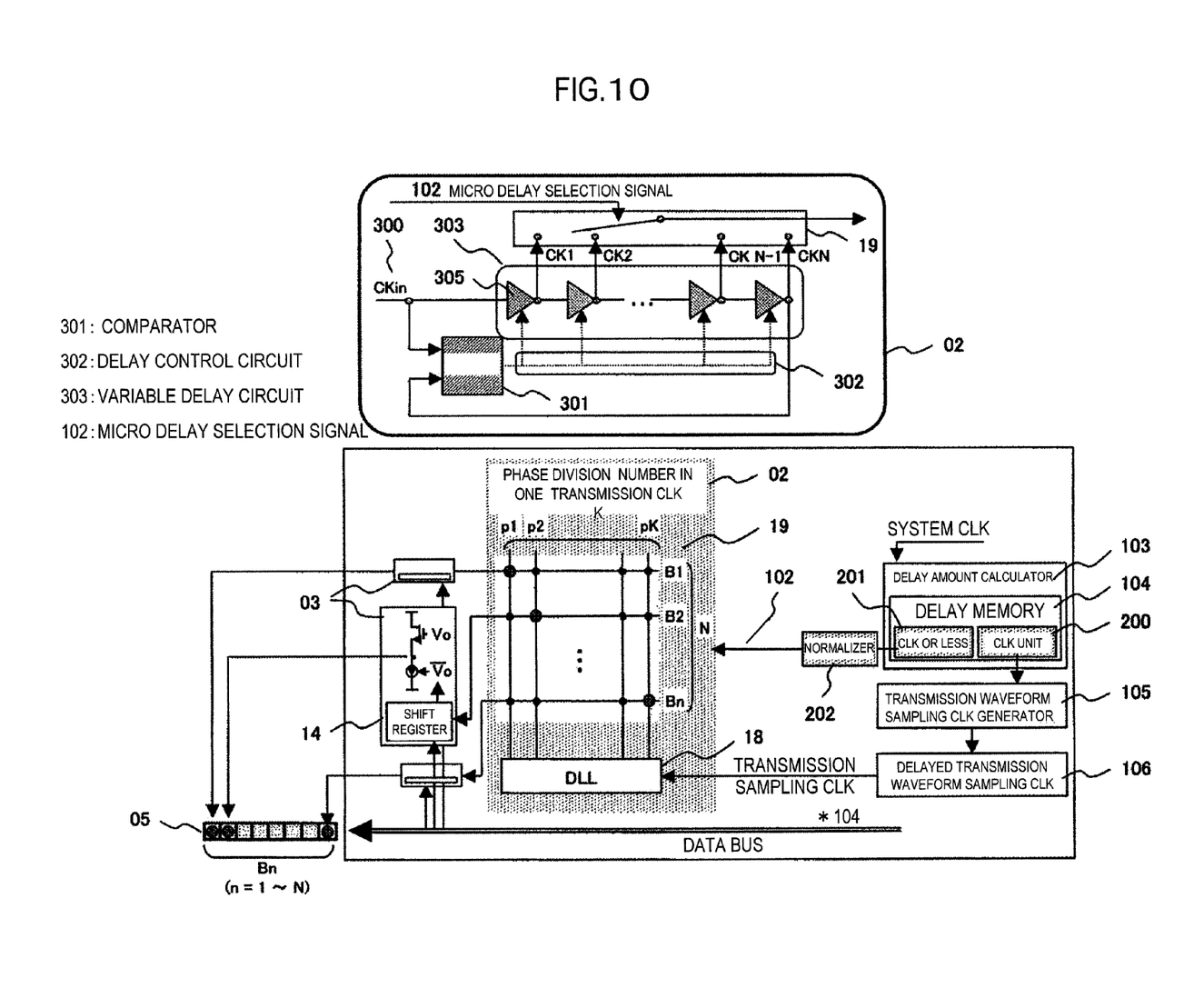
FIG. 10 is a block diagram showing an embodiment of creating a micro delay selection signal and a transmission sampling CLK.

FIG. 10 shows an embodiment of creating a micro delay selection signal and a transmission sampling CLK.

The transmission signal delay process includes two steps. One is to apply a delay amount in unit of a system clock (the delay amount is stored in a memory area 200) and the other is to apply a delay amount equal to or smaller than the unit of the system clock (the delay amount is stored in a memory area 201).

The delay amount necessary for phasing the signals of each channel is calculated by a delay amount calculator 103 and the calculation results are stored in a delay memory 104. Alternatively, the delay amount may be calculated by a system outside the ultrasonic diagnostic apparatus, and only the results thereof may be transmitted to the delay memory 104. In the delay memory 104, memory areas 200 and 201 for storing a delay (coarse delay) in units of the system CLK and a delay equal to or smaller than that of the system CLK are provided. This is only an example, and the respective values may not be stored in the memory, but may be maintained in a system. A transmission waveform sampling CLK generator 105 generates the sampling CLK of a transmission signal, and the sampling CLK is selected arbitrarily. For example, in order to generate a 2-MHz/3-wave transmission signal, at least six 4-MHz sampling CLKs are required. The number of clocks can be appropriately selected for each application as needed.

The transmission waveform sampling CLK generator 105 receives the delay data in units of the system CLK necessary for each channel from the delay memory 104 and generates a delayed waveform sampling CLK 106.

The delayed waveform sampling CLK is input to the DLL circuit 18. The DLL circuit 18 outputs a transmission sampling CLK to each channel at timings corresponding to the equal division of the system CLK by a predetermined phase division number K within one transmission CLK. Which timing signal will be obtained among the K divisions is determined based on data stored in the memory area 201 of the delay memory 104. The value stored in the memory area 201 is normalized to the division number K of the system CLK by a normalizer 202 and transmitted to the selector circuit 19 as a micro delay selection signal 102. In this way, a micro delay amount for each channel is selected, and as a result, the transmission waveform sampling CLK delayed in unit of the system CLK is output with a delay precision equal to or smaller than the unit of the system CLK unit. The CLK is input to the shift register 14, and the transmission waveform data having been transmitted in advance thereto are read, whereby transmission waveforms delayed optimally for each channel can be generated.

Since the transmission circuit 03 is supposed to be built into the probe, a configuration in which only an NMOS transistor as shown in FIG. 10 is used can be considered, for example. The major part of the transmission circuit 03 includes an NMOS source follower and an NMOS switch that operates only at the falling edges.

Hereinabove, the invention has been described based on the configuration shown in FIG. 1. In the present embodiment, the transmission circuit 03 can be provided uniquely to each transducer 05. Moreover, since the transmission signal generator 14 and the transmission phasing circuit 02 can be formed at the same time, an analog signal cable through which the ultrasonic diagnostic apparatus main body 100 transmits a high-voltage transmission signal to the probe 01 as in the related art is not necessary.

Second Embodiment

Figure 2:
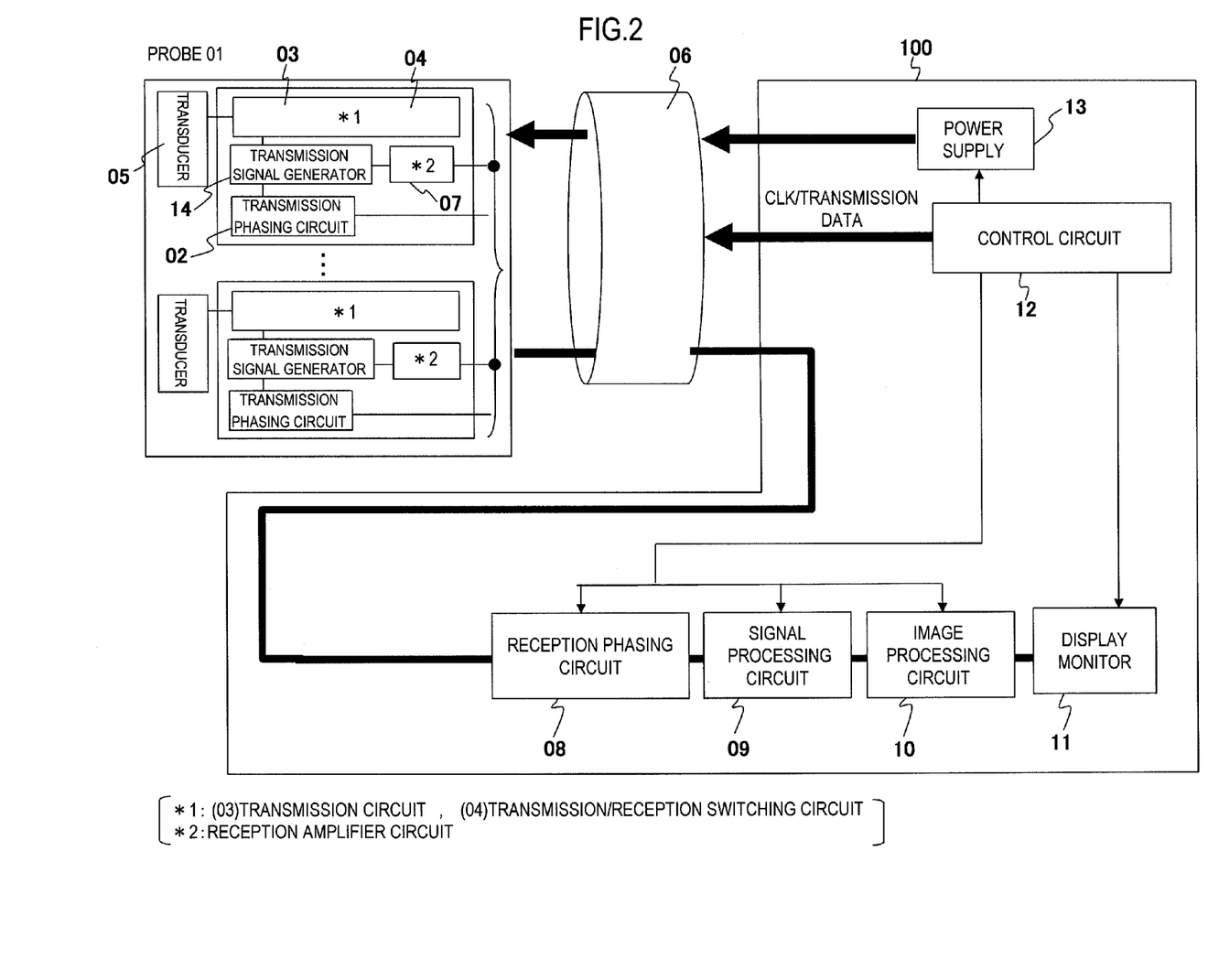
FIG. 2 is a block diagram of an ultrasonic diagnostic apparatus according to a second embodiment of the invention.

FIG. 2 shows the second embodiment of the invention. In the present embodiment, the reception amplifier circuit 07 is incorporated into the probe 01 together with the transmission circuit 03.

In this case, the transmission circuit 03 and the reception amplifier circuit 07 can be provided uniquely to each transducer 05.

Third Embodiment

Figure 3:
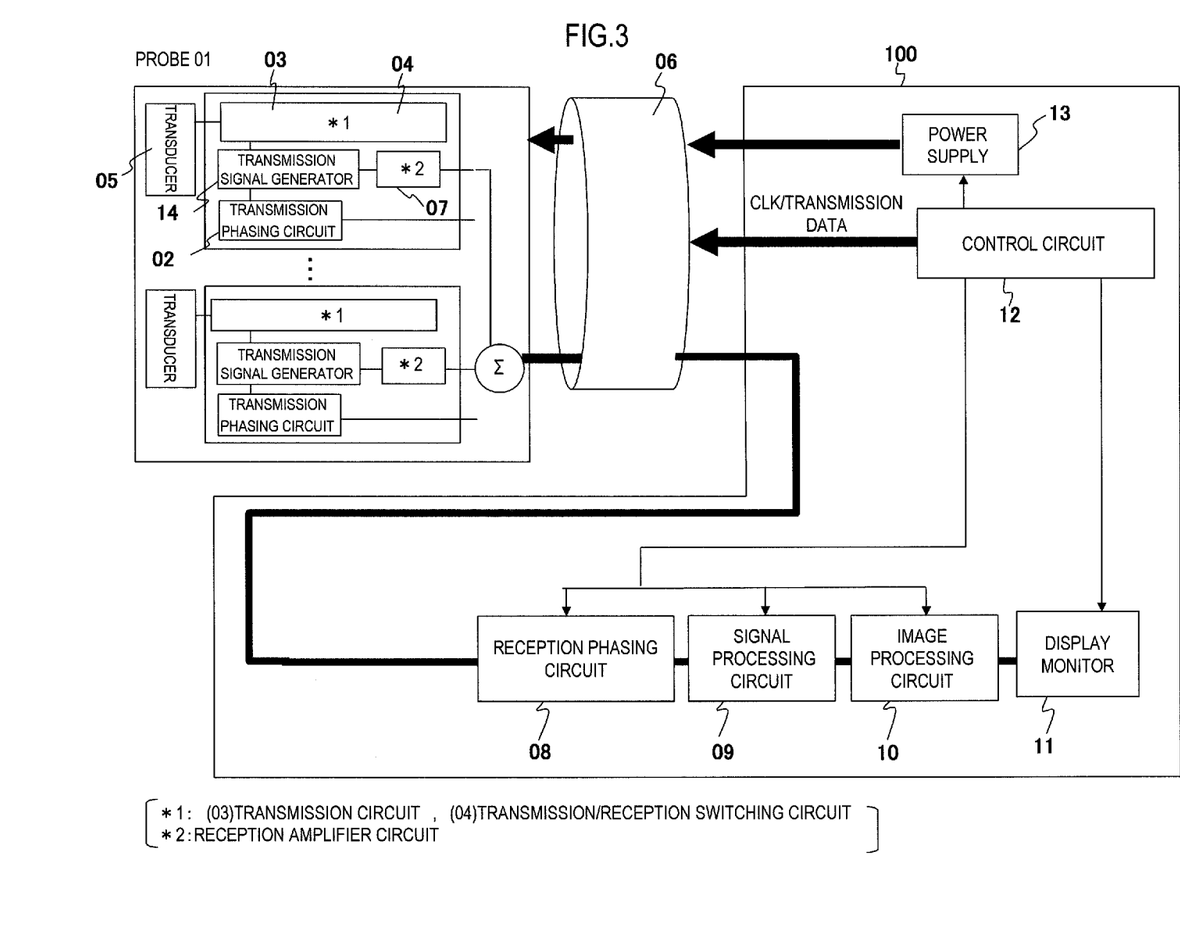
FIG. 3 is a block diagram of an ultrasonic diagnostic apparatus according to a third embodiment of the invention.

FIG. 3 shows the third embodiment of the invention. When the number of transducers 05 increases, so that it is difficult to transmit all signals output by the reception amplifier circuit 07 as described in the second embodiment to the ultrasonic diagnostic apparatus main body 100 through a cable, some of the signals output by the reception amplifier circuit 07 are added by an adder circuit 15 and transmitted to the main body 100.

In the present embodiment, it is possible to decrease the number of transmission cables through which the probe 01 transmits signals to the ultrasonic diagnostic apparatus main body.

Fourth Embodiment

Figure 11:
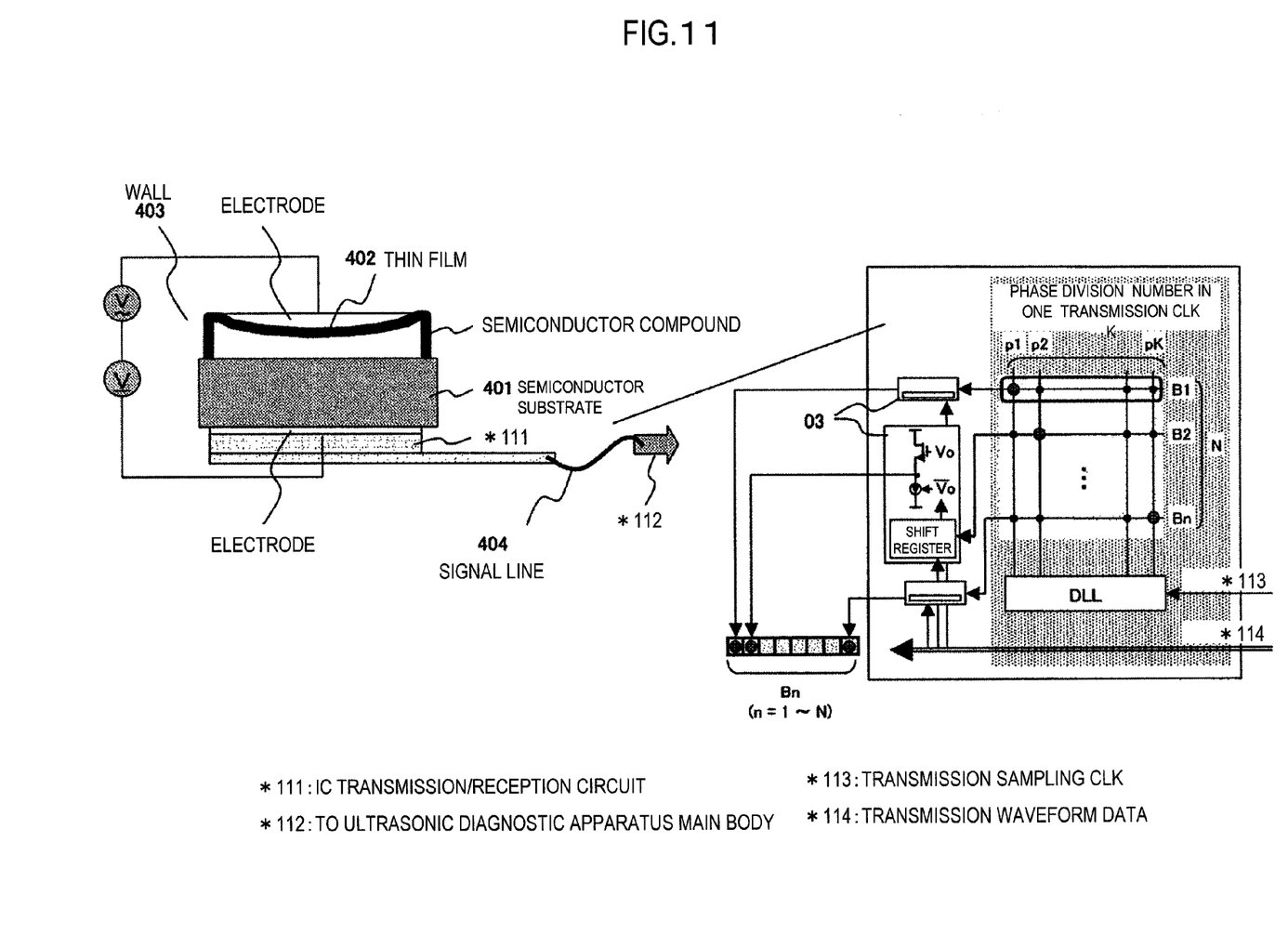
FIG. 11 is a block diagram of an ultrasonic diagnostic apparatus according to a fourth embodiment of the invention.

FIG. 11 shows an example in which a transmission amplifier circuit which has the transmission phasing function according to the invention and can be incorporated into a probe is mounted on a CMUT (Capacitive Micromachined Ultrasonic Transducer).

The CMUT is configured to include a semiconductor substrate 401, a thin film 402 made of semiconductor compounds, and a wall 403, and a space surrounded by these elements is under vacuum or filled with a certain gas.

The CMUT has just the same electrical structure as a capacitor. A bias voltage is applied to the semiconductor substrate 401 and the semiconductor thin film 402 to produce an electric field, and the degree of tension of the semiconductor thin film 402 is controlled by the electric field. In this state, when an electrical signal having an ultrasonic frequency is applied, the thin film is excited, and ultrasonic waves corresponding to the magnitude of the applied bias voltage are excited by an electroacoustic conversion effect.

A semiconductor substrate 401 in which the proposed circuit is mounted under the electrode on the lower side of the semiconductor substrate shown in FIG. 11 is produced by a semiconductor circuit manufacturing method. For example, a signal line 404 or the like on the lower surface of the circuit substrate is connected to the ultrasonic diagnostic apparatus main body through a cable.

As in the present embodiment, when the invention is applied to a probe as typified by the CMUT, manufactured by a semiconductor manufacturing method, it is possible to easily integrate and mount the proposed circuit.

REFERENCE SIGNS LIST

01 Probe
02 Transmission Phasing Circuit
03 Transmission Circuit
04 Transmission/Reception Switching Circuit
05 Transducer
06 Probe Cable
07 Reception Amplifier Circuit
08 Reception Phasing Circuit
09 Signal Processing Circuit
10 Image Processing Circuit
11 Display Monitor
12 Control Circuit
13 Power Supply
14 Transmission Signal Generator
15 Adder Circuit
16 Focus Point F
17 Delay Memory
18 DLL Circuit
19 Selector Circuit
100 Ultrasonic Diagnostic Apparatus Main Body
101 Data Bus
102 Micro Delay Selection Signal 103 Delay Amount Calculator
104 Delay Memory
105 Transmission Waveform Sampling CLK Generator
106 Transmission Waveform Sampling CLK
200 Memory Area Equivalent to CLK Unit
201 Memory Area Smaller Than CLK Unit
202 Normalizer
300 Signal Input Portion
301 Phase Comparator
302 Delay Control Circuit
303 Variable Delay Circuit
304 Feedback Signal
305 Delay Element
401 Semiconductor Substrate
402 Thin Film
403 Wall
404 Signal Line

The invention claimed is:

1. An ultrasonic diagnostic apparatus comprising:
a probe which has a transducer and which transmits and receives ultrasonic waves; and
an ultrasonic diagnostic apparatus main body,
wherein signals are transmitted and received between the ultrasonic diagnostic apparatus main body and the probe,
wherein the probe includes a transmission signal generator that generates an ultrasonic transmission signal, a transmission circuit that amplifies the generated transmission signal, and a transmission phasing circuit that adjusts the timing of the transmission signal, and
wherein the transmission phasing circuit includes a DLL (Delay Locked Loop) circuit that generates a micro delay less than or equal to the cycle of a transmission clock signal and a selector circuit that selects and outputs the output of the DLL circuit.

2. The ultrasonic diagnostic apparatus according to claim 1,
wherein the probe includes a plurality of transducers, and
wherein transmission signal generator, the transmission circuit, and the transmission phasing circuit are independently provided to each transducer.

3. The ultrasonic diagnostic apparatus according to claim 1, wherein the signals are transmitted and received between the ultrasonic diagnostic apparatus main body and the probe through a digital transmission cable or wireless transmission.

4. The ultrasonic diagnostic apparatus according to claim 1, wherein the transmission signal generator has a memory for storing transmission signal waveforms.

5. The ultrasonic diagnostic apparatus according to claim 4, wherein the memory for storing the transmission signal waveforms is a shift register.

6. The ultrasonic diagnostic apparatus according to claim 1, wherein a reception amplifier circuit is incorporated into the probe.

7. The ultrasonic diagnostic apparatus according to claim 6, wherein the output of the reception amplifier circuit is added by an adder circuit and transmitted to the ultrasonic diagnostic apparatus main body.

8. The ultrasonic diagnostic apparatus according to claim 1, wherein the transducer is a CMUT (Capacitive Micromachined Ultrasonic Transducer).

9. The ultrasonic diagnostic apparatus according to claim 8, wherein the transmission signal generator, the transmission circuit, and the transmission phasing circuit are mounted on a substrate of the CMUT by a semiconductor circuit manufacturing method.

10. An ultrasonic diagnostic apparatus comprising:
a probe which has a transducer and which transmits and receives ultrasonic waves; and
an ultrasonic diagnostic apparatus main body,
wherein signals are transmitted and received between the ultrasonic diagnostic apparatus main body and the probe,
wherein the probe includes a transmission signal generator that generates an ultrasonic transmission signal, a transmission circuit that amplifies the generated transmission signal, and a transmission phasing circuit that adjusts the timing of the transmission signal, and
wherein the transmission phasing circuit includes a delay memory that stores a delay amount in unit of a principal clock, a DLL (Delay Locked Loop) circuit that generates a micro delay less than or equal to the principal clock, and a selector circuit that selects and outputs the output of the DLL circuit.

11. The ultrasonic diagnostic apparatus according to claim 10, wherein the DLL circuit includes a phase comparator, a delay control circuit, and a variable delay circuit, the phase comparator compares the phase of an input signal and the phase of the output of the variable delay circuit, the delay control circuit receives the result of comparison by the phase comparator and controls a delay amount of the variable delay circuit, and the variable delay circuit delays the input signal in accordance with the output of the delay control circuit.

12. The ultrasonic diagnostic apparatus according to claim 11, wherein the variable delay circuit includes a plurality of series-connected inverters and outputs the delay signal as the output of the respective inverters.

13. A ultrasonic diagnostic method comprising:
transmitting and receiving ultrasonic waves by a transducer in a probe;
transferring signals between the probe and an ultrasonic diagnostic apparatus main body;
generating an ultrasonic transmission signal within the probe;
adjusting, by a transmission phasing circuit, the timing of the transmission signal, the transmission phasing circuit including a DLL (Delay Locked Loop) circuit and a selector circuit;
generating, by the DLL circuit, a micro delay less than or equal to the cycle of a transmission clock signal;
selecting and outputting, by the selector circuit, the output of the DLL circuit; and
amplifying the transmission signal of which the timing is adjusted.

* * * * *